United States Patent

Nierlich et al.

[11] Patent Number: 5,994,601
[45] Date of Patent: Nov. 30, 1999

[54] PROCESS FOR PREPARING BUTENE OLIGOMERS FROM FISCHER-TROPSCH OLEFINS

[75] Inventors: Franz Nierlich; Walter Toetsch, both of Marl; Paul Olbrich, Haltern; Wilhelm Droste; Richard Mueller, both of Marl, all of Germany

[73] Assignee: Huels Aktiengesellschaft, Marl, Germany

[21] Appl. No.: 08/899,819

[22] Filed: Jul. 24, 1997

[30] Foreign Application Priority Data

Jul. 24, 1996 [DE] Germany .......................... 196 29 906

[51] Int. Cl.⁶ ..................................... C07C 1/00
[52] U.S. Cl. .................... 585/329; 585/510; 585/518; 585/519; 585/520; 518/726
[58] Field of Search .................. 585/329, 510, 585/518, 519, 520; 518/726

[56] References Cited

U.S. PATENT DOCUMENTS

| | | | |
|---|---|---|---|
| 4,046,829 | 9/1977 | Ireland et al. | 260/676 |
| 4,052,477 | 10/1977 | Ireland et al. | 260/676 |
| 4,279,830 | 7/1981 | Haag et al. | 585/500 |
| 4,482,775 | 11/1984 | Smith, Jr. | 585/510 |
| 4,731,490 | 3/1988 | Coughenour et al. | 585/329 |
| 5,023,389 | 6/1991 | Grandvallet et al. | 585/329 |
| 5,177,282 | 1/1993 | Nierlich et al. | 585/329 |

FOREIGN PATENT DOCUMENTS

| | | |
|---|---|---|
| 0 216 972 | 4/1987 | European Pat. Off. . |
| 0 221 206 | 5/1987 | European Pat. Off. . |
| 0 233 302 | 8/1987 | European Pat. Off. . |
| 0 395 857 | 11/1990 | European Pat. Off. . |
| 2 029 624 | 3/1971 | Germany . |
| 2 347 235 | 4/1974 | Germany . |
| 28 55 423 | 7/1979 | Germany . |
| 1600 37 | 4/1983 | Germany . |
| 8500429 | 4/1986 | Netherlands . |

OTHER PUBLICATIONS

S. T. Bakas, et al., AIChE Summer Meeting, pp. 1–32, Aug. 19–22, 1990, "Production Of Ethers From Field Butanes And Refinery Streams".

A. Barth, et al., Z. Anorg. Allg. Chem., vol. 521, pp. 207–214, 1985, "Die Reduzierbarkeit Des $Ni^{2+}$ Durch Niedere Olefine Und Die Dimerisierungsaktivitaet Der $Ni^{2+}$ Ausgetauschten Zeolithe".

Y. Chauvin, et al., Jahrgang. Heft, vol. 7/8, pp. 309–315, Jul./Aug. 1990, "Upgrading of $C_2$, $C_3$, and $C_4$ Olefins by IFP Dimersol Technology".

(List continued on next page.)

*Primary Examiner*—Marian C. Knode
*Assistant Examiner*—In Suk Bullock
*Attorney, Agent, or Firm*—Oblon, Spivak, McClelland, Maier & Neustadt, P.C.

[57] ABSTRACT

A process is described in which butene oligomers are prepared from Fischer-Tropsch olefins, in which the butenes present in a $C_4$ fraction of Fischer-Tropsch hydrocarbons are oligomerized to obtain dibutene. The dibutene can be fractionated in a fine distillation stage into di-n-butene and di-isobutene. In one embodiment of the process, the ethylene present in the Fischer-Tropsch olefins is dimerized and the dimerization mixture is recycled to the $C_4$ fraction. In another embodiment, the isobutene present in the $C_4$ fraction is reacted with an alcohol to give an alkyl tert-butyl ether, and only the remaining n-butene is oligomerized so that di-n-butene is formed as the sole dibutene.

21 Claims, 2 Drawing Sheets

OTHER PUBLICATIONS

R. L. Espinoza, et al., Applied Catalysis, vol. 31, pp. 259–266, 1987, "Catalytic Oligomerization Of Ethene Over Nickel–Exchanged Amorphous Silica–Alumina; Effect Of The Nickel Concentration".

H. W. Grote, The Oil and Gas Journal, pp. 73–76, Mar. 31, 1958, "Introducing: Alkar And Butamer".

F. Nierlich, Huels Publication, Clean Fuel Technology, Hydrocarbon Processing, 2 pages, Feb. 1992, "Oligomerize For Better Gasoline".

F. Nierlich, Huels Publication, Oil Gas Refining, 6 pages, Oct. 15–16, 1992, "Recent Developments In Olefin Processing For Cleaner Gasoline".

F. Nierlich, et al., Huels Publication, Erdol & Kohle, Erdgas, 6 pages, Feb. 1986, "Verfahren Zur Selektiven Hydrierung Mehrfach Ungesaettigter Kohlenwasserstoffe In Olefin–Gemischen" (with English Abstract).

F. Nierlich, Erdol & Kohle, Erdgas Petrochemie, AIChE 1987 Summer National Meeting, 4 pages, Aug. 16–19, 1987, "Intgrated Tert. Butyl Alcohol/Di–n–Butenes Production From FCC $C_4$'s".

R.A. Pogliano, et al., Petrochemical Review, pp. 1–22, Mar. 19–21, 1996, "Dehydrogenation–Based Ether Production Adding Value To LPG And Gas Condensate".

Bernhard Scholz, et al., Methyl Tert–Butyl Ether, vol. A 16, pp. 543–550, "Methyl Tert–Butyl Ether".

G. C. Sturtevant, et al., UOP Technology Conference, pp. 2,4,6,8,10,12,14,16 and 18, 1988, "Oleflex Selective Production Of Lights Olefins".

K. H. Walter, et al., DGMK–Conference, 34 pages, Nov. 11–12, 1993, "Selective Hydrogenation And Dehydrogenation".

PROCESS FOR PREPARING BUTENE OLIGOMERS FROM FISCHER-TROPSCH OLEFINS

BACKGROUND OF THE INVENTION

1. Field of the Invention

The invention relates to a process for preparing butene oligomers from Fischer-Tropsch olefins.

2. Discussion of the Background

Butene oligomers are valuable starting materials for preparing alcohols. Of the oligomeric butenes, the preferred butene oligomers are the isomeric octenes. Isomeric octenes are butene dimers and are therefore also called dibutene.

Dibutene is an isomeric mixture which is formed by the dimerization or codimerization of butenes, i.e., of n-butene and/or isobutene. The dimerization product of n-butene. i.e., 1-butene or 2-butene, is termed di-n-butene. Significant components of di-n-butene are 3-methyl-2-heptene, 3,4-dimethyl-2-hexene and, to a lesser extent, n-octenes. Di-isobutene is the isomeric mixture which is formed by dimerization of isobutene. Di-n-butene, dibutene, and diisobutene are therefore distinguished by their degree of branching. Di-isobutene contains more highly branched molecules than dibutene, and dibutene is more highly branched than di-n-butene.

Dibutene, di-n-butene, and di-isobutene are starting materials for the preparation of isomeric nonanols by hydroformylation to the $C_9$ aldehyde, followed by hydrogenation to the alcohol. Esters of these nonanols, in particular the phthalic esters, are plasticizers, which are primarily used in poly(vinyl chloride). Nonanols from di-n-butene are more linear (less branched) than nonanols from dibutene, which in turn are more linear than nonanols from di-isobutene. Nonanol esters derived from di-n-butene have, precisely because of their highly linear structure, greater application advantages than the more highly branched esters derived from dibutene- and diisobutene-based nonanols.

As starting materials for the dimerization reactions, butenes can be produced from the $C_4$ fraction of steam crackers or FC crackers. The $C_4$ fraction is generally worked up by first removing or separating 1,3-butadiene by selective scrubbing, e.g., using n-methylpyrrolidone. Then, isobutene is typically removed from the $C_4$ fraction after the 1,3-butadiene has been removed. Isobutene is a desirable and particularly valuable component of the $C_4$ fraction because it can be reacted with isobutane to give high-octane isooctane or with an alkanol, such as methanol, to give methyl tert-butyl ether (MTBE), which, as an additive to motor gasoline, improves its octane rating. As stated, isobutene is in demand as a cracking product, it is not generally available for an oligomerization process.

After the reaction of the isobutene, n-butene, n-butane, and isobutane remain behind in the $C_4$ fraction. However, the proportion of n-butene in the cracked products of a steam cracker or an FC cracker is relatively low, on the order of barely 10% by weight, based on the chief target product ethylene. Thus, a steam cracker having the respectable capacity of 600,000 metric t/year of ethylene produces only around 60,000 metric t/year of n-butenes. Although the amount of both n-butene and isobutene could be increased by dehydrogenating around 15,000 metric t/year of n-butane and isobutane that arise in addition to n-butene, it is not feasible, because such dehydrogenation plants require high capital costs and are therefore uneconomic for such a small capacity.

The amount of n-butenes which arise directly in a steam cracker or an FC cracker is therefore insufficient to produce a sufficient quantity of dibutene for a nonanol plant, whose capacity is so high that it could compete economically with the existing large-scale plants for producing important plasticizer alcohols, such as 2-ethyl hexanol. In order to cover the dibutene requirement of a large nonanol plant, n-butene would have to be collected from several steam or FC crackers and jointly oligomerized. Alternatively, an unfractionated $C_4$ fraction could be collected from several steam or FC crackers and worked up to n-butene on site. However, the transport of liquid gases is expensive and complex safety precautions are required.

On an industrial scale, over 400,000 metric t/year of ethylene and 500,000 metric t/year of propylene are prepared by optimized Fischer-Tropsch processes in the Union of South Africa. A major disadvantage in these processes is the unavoidable production of large amounts of higher hydrocarbons and, in particular, of $C_4$ hydrocarbons for which, apart from as additive to internal combustion fuels, there is virtually no suitable use. However, even in fuel, the $C_4$ fraction is somewhat unsuitable because of its high content of olefins, which have a tendency to form gums, and because of its high vapor pressure, which contributes to environmental pollution.

In general, there are no known feasible processes for producing butenes and butane oligomers at a single site in amounts sufficient to supply, e.g., a large nonanol plant.

SUMMARY OF THE INVENTION

One object of the present invention is to provide a process for preparing butene oligomers wherein valuable di-n-butene can be separated off from the dibutene.

Another object of the present invention is to provide a process that could be controlled in such a manner that, in addition to higher butene oligomers, di-n-butene is formed as the sole dibutene.

Another object of the present invention is to provide a process for preparing di-n-butene and higher butene oligomers in which alkyl tert-butyl ethers are obtained as desirable by-products.

Another object of the present invention is to provide a process for oligomerization which will use butenes that are unavoidably produced in a process directed at other olefins, and by this add value to the process.

Another object of the present invention is to provide a process for preparing butenes at a single site without the need for transport over great distances.

Another object of the present invention is to provide a process for preparing at a single site the amounts of butenes for oligomerization as are required for the operation of a large plant for the preparation of nonanols, i.e., at a capacity of 200,000 to 800,000 metric t/year.

Another object of the present invention is to provide a process in which the quantitative ratio of these products could be controlled.

These and other objects of the present invention have been achieved by oligomerizing butenes that are present in a $C_4$ fraction obtained from a Fischer-Tropsch process, wherein dibutene is obtained.

One embodiment of the present invention is a process for preparing butene oligomers from Fischer-Tropsch hydrocarbons, which includes:

separating from Fischer-Tropsch hydrocarbons a $C_4$ fraction containing butenes; and oligomerizing said butenes with a catalyst to obtain an oligomerization mixture containing dibutene.

Another embodiment of the present invention is a process for preparing butene oligomers from Fischer-Tropsch hydrocarbons, which includes:

separating from Fischer-Tropsch hydrocarbons a $C_4$ fraction containing butenes, said butenes comprising n-butenes and isobutene;

etherifying said isobutene by reacting with an alkanol over a first catalyst to obtain alkyl tert-butyl ether; and oligomerizing said n-butenes with a second catalyst to obtain an oligomerization mixture containing di-n-butene.

Another embodiment of the present invention is a process for preparing butene oligomers from Fischer-Tropsch hydrocarbons, which includes:

separating from Fischer-Tropsch hydrocarbons a $C_4$ fraction containing butenes, said butenes comprising n-butenes and isobutene;

etherifying said isobutene by reacting with an alkanol over a first catalyst to obtain alkyl tert-butyl ether;

oligomerizing said n-butenes with a second catalyst to obtain an oligomerization mixture containing di-n-butene; and isomerizing with a third catalyst a portion of n-butenes that remain after said oligomerizing to obtain isobutene.

By the present invention, formerly unsuitable $C_4$ fractions produced by the Fischer-Tropsch process may be put to use in the oligomerization reaction to produce valuable product, such as dibutene, di-n-butene, and alkyl tert-butyl ether. By the present invention, these products can be produced in amounts which are sufficient to support a large capacity nonanol plant, and thereby add value to a Fischer-Tropsch process.

BRIEF DESCRIPTION OF THE DRAWINGS

A more complete appreciation of the invention and many of the attendant advantages thereof will be readily obtained as the same becomes better understood by reference to the following detained description when considered in connection with the accompanying drawings.

DESCRIPTION OF THE PREFERRED EMBODIMENTS

Figure 1:
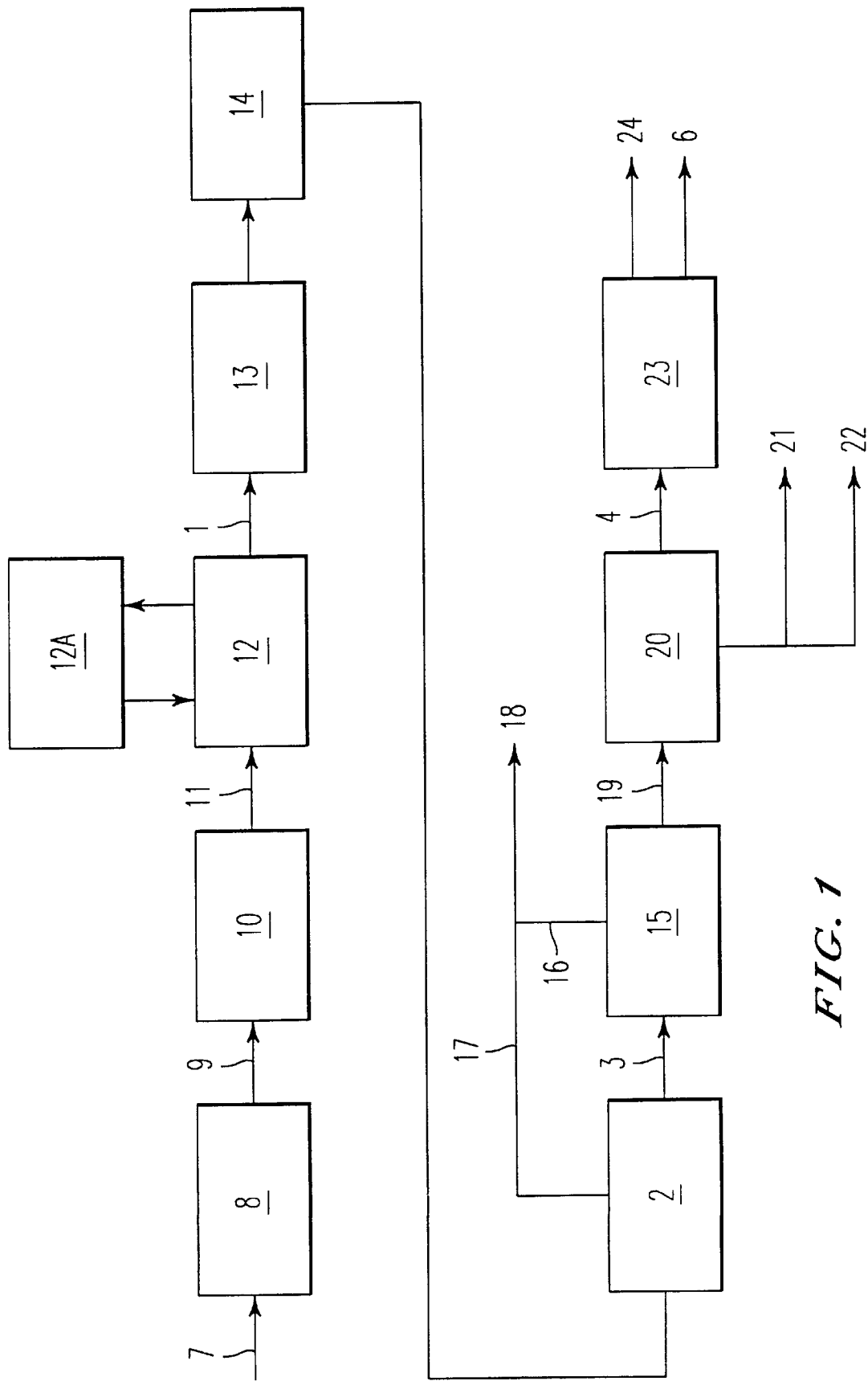
FIG. 1 is a block diagram which depicts Variant A.

Other features of the invention will become apparent in the course of the following descriptions of exemplary embodiments which are given for illustration of the invention and are not intended to be limiting thereof.

The process according to the invention starts from a $C_4$ fraction 1, which originates from the Fischer-Tropsch process, in which, as is known, hydrocarbons or oxygen-containing products are produced from synthesis gas (CO/$H_2$). Synthesis gas can be prepared form the most diverse energy carriers, such as natural gas, fuel oil and residue oil, brown coal and bituminous coal, in virtually any desired quantities.

Whereas the Fischer synthesis was originally designed for the preparation of gasoline after the Second World War, interest was primarily concentrated on the development of processes which lead to $\alpha$-olefin-rich fractions of hydrocarbons having a low carbon number. In the latter case, in a similar manner to the case of steam crackers, the optimization of the ethylene yield, but also the propylene yield, plays a major role, because these olefins are base components for many important chemical products, such as polyethylene, polypropylene, poly(vinyl chloride) and ethylene oxide and propylene oxide.

Predominantly olefinic short-chain hydrocarbons having 2 to 6 carbon atoms, in particular, $\alpha$-olefins, are successfully prepared, e.g., by the process according to EP-A1-0 216 972, the entire contents of which are hereby incorporated by reference. Its essential feature is the choice of a defined catalyst, namely a single-phase, carbide-containing and reduced support-free spinel, which is formed from an oxidic precursor substance of the empirical formula $Fe_xCo_yO_4$, in which x and y are integers or decimal numbers, with the provision that the sum x+y is 3 and the ratio x/y is at least 7. The catalyst has a surface area of at least about 0.1 m$^2$/g and up to 5 m$^2$/g, and it can contain as promoter a compound of a metal of group IA or IIA of the Periodic Table of the Elements.

The catalyst is pyrophoric and is therefore deactivated by small amounts of oxygen in an inert gas for improved handling. It can be used as a suspension in an inert organic liquid, such as high-boiling paraffins, aromatic hydrocarbons or ethers, tertiary amines or mixtures of such substances, in amounts of 10 to 50 g of dry catalyst per 500 g of organic liquid. Prior to introduction of synthesis gas, the catalyst is conditioned, i.e., reactivated, by flushing with nitrogen and treating with hydrogen at elevated temperature.

The CO/$H_2$ ratio in synthesis gas can fluctuate in broad ranges and is advantageously between 1:1 and 2:1. The optimum temperature for producing the desired short-chain $\alpha$-olefins having 2 to 6 carbon atoms is 230 to 270° C., in particular 240 to 260° C. This temperature is critical, because at higher temperatures more methane is formed, whereas at lower temperatures the formation of waxy products is favored. The process is generally carried out at a pressure in the range 350 to 2200 kPa.

Under similar conditions, in the fixed-bed process the catalyst also preferentially produces $C_2$ to $C_6$ hydrocarbons, which are predominantly olefins and are preferably $\alpha$-olefins. From the hydrocarbon mixture, the $C_4$ fraction is separated off in a customary manner, advantageously by fractional distillation at low temperature and/or elevated pressure.

The invention is preferably a process for preparing butene oligomers from Fischer-Tropsch olefins, in which the butenes present in the $C_4$ fraction 1 of Fischer-Tropsch olefins are oligomerized in the oligomerization stage 2 and dibutene 4 is produced from the oligomerization mixture 3.

It may be emphasized that a suitable source of the $C_4$ fraction 1 is any desired $C_4$ fraction that originates from the Fisher-Tropsch process.

Variant A

Variant A is described in FIG. 1.

Synthesis gas 9 of appropriate composition is produced from the energy carrier 7 in the synthesis gas stage 8 and passed into the Fisher-Tropsch synthesis stage 10, in which an olefin-rich hydrocarbon mixture 11 having high contents in the range $C_2$ to $C_6$ is produced, for example by the process of EP-A1 216 972. The $C_4$ fraction 1 is produced therefrom in the $C_4$ fraction separation stage 12 in a customary manner, e.g., by liquifying the gaseous portions at −30° C. and fractional distillation. This produces a $C_4$ fraction 1, which generally has the following composition:

| 1-Butene | 70 ± 10% |
| --- | --- |
| Isobutene | 10 ± 5% |
| 2-Butene | 10 ± 5% |
| N-butane/isobutane | 12 ± 3% |
| 1,3-butadiene | Traces |

The yield of $C_4$ fraction 1 can be increased by dimerizing the ethylene arising in the $C_4$ fraction separation stage 12 in the dimerization stage 12a. The Dimersol® process, for example, is suitable for this, which was described by Y. Chauvin et al. in Erdöl Erdgas Kohle, 106, 7/8 (1990), pages 309 ff, the entire contents of which are hereby incorporated by reference. The process operates in the liquid phase with a catalyst of the nickel-compound-based Ziegler catalyst type, which is activated by an organometallic compound. The "degenerate polymerization" to give the dimer proceeds under mild conditions at about 20 to 80° C., and the conversion rates per pass are 50 to 90%. The dimerization mixture is recycled to the $C_4$ fraction separation stage 12.

The $C_4$ fraction 1 contains traces of 1,3-butadiene. It is advisable to remove these dienes since, even in very low amounts, they can damage the oligomerization catalyst. A suitable process is the selective hydrogenation 13, which, in addition, increases the proportion of the desired n-butene. A suitable process has been described, for example, by F. Nierlich et al. in Erdöl & Kohle, Erdgas, Petrochemie, 1986, pages 73 ff, the entire contents of which are hereby incorporated by reference. It operates in the liquid phase with completely dissolved hydrogen in stoichiometric amounts. Suitable selective hydrogenation catalysts are, for example, nickel and, in particular, palladium on a support, e.g., 0.3% by weight palladium on activated carbon or, preferably, on aluminum oxide. A small amount of carbon monoxide in the ppm range promotes the selectivity of hydrogenation of the 1,3-butadiene to the monoolefin and counteracts the formation of polymers, the so-called "green oil", which then deactivates the catalyst. The process operates at room temperature or moderately elevated temperatures up to 60° C. and under elevated pressures, which are expediently in the range from up to 20 bar. The content of 1,3-butadiene in the $C_4$ fraction 1 is decreased in this manner to values of <1 ppm, which no longer interfere in the oligomerization.

It is further expedient to pass the then substantially 1,3-butadiene-free $C_4$ fraction 1, upstream of entry into the oligomerization stage 2, through the purification stage 14, a molecular sieve, which removes other substances which are harmful to the oligomerization catalyst and further increases its service life. These harmful substances include oxygen compounds and sulfur compounds. The purification using molecular sieves has been described by F. Nierlich et al. in EP-B1 395 857, the entire contents of which are hereby incorporated by reference. A molecular sieve having a pore diameter of 4 to 15 angstroms, advantageously 7 to 13 angstroms, is expediently used. In some cases, it is expedient for economic reasons to pass the dehydrogenation mixture successively through molecular sieves having different pore sizes. The process can be carried out in the gas phase, in liquid phase, or in gas-liquid phase. The pressure is accordingly generally 1 to 200 bar. It is expedient to employ room temperature or elevated temperatures up to 200° C.

The chemical nature of the molecular sieves is less important than their physical properties, i.e., in particular the pore size. The most varied types of molecular sieves can therefore be used, both crystalline natural aluminum silicates, e.g., sheet lattice silicates, and synthetic molecular sieves, e.g., those having zeolite structure. Zeolites of the A, X and Y type are obtainable, inter alia, from Bayer AG, Dow Chemical Co., Union Carbide Corporation, Laporte Industries Limited and Mobile Oil Co. Suitable synthetic molecular sieves for the process are those which, in addition to alumina and silicon, further contain other atoms introduced by cation exchange, such as gallium, indium or lanthanum, or nickel, cobalt, copper, zinc or silver. In addition, synthetic zeolites are suitable in which, in addition to aluminum and silicon, other atoms such as boron or phosphorus have further been incorporated into the lattice by mixed precipitation.

As already stated, the selective hydrogenation stage 13 and the purification stage 14 with a molecular sieve are optional advantageous measures for the process according to the invention. In principle, they can be in any order, but the order specified in FIG. 1 is preferred.

The $C_4$ fraction 1, which if appropriate is pretreated in the described manner, is passed into the oligomerization stage 2 which is an essential part of the process according to the invention. The oligomerization is a co-oligomerization of n-butene and isobutene and has been described by F. Nierlich in Oligomerization for Better Gasoline, Hydrocarbon Processing, 1992, pages 45 ff., or by F. Nierlich et al., the entire contents of which are hereby incorporated by reference, in the previously mentioned EP-B1 0 395 857. The procedure is generally carried out in the liquid phase and employs, e.g., as homogeneous catalyst, a system which consists of nickel (II) octoate, ethylaluminum chloride and a free fatty acid (DE-C-28 55 423, the entire contents of which are hereby incorporated by reference), or preferably uses one of the numerous known fixed catalysts or catalysts suspended in the oligomerization mixture which are based on a nickel and silicon. The catalysts frequently additionally contain aluminum. Thus, DD-PS 160 037, the entire contents of which are hereby incorporated by reference, describes the preparation of a precipitated catalyst containing nickel and aluminum on silicon dioxide as support material. Other useful catalysts are obtained by exchanging positively charged particles, such as protons or sodium ions, situated on the surface of the support materials, against nickel ions. This succeeds with the most varied support materials, such as amorphous aluminum silicate (R. Espinoza et al., Appl. Kat., 31 (1987) pages 259–266; crystalline aluminum silicate (DE-C-20 29 624; zeolites of the ZSM type (Netherlands patent 8 500 459); an X-zeolite (DE-C-23 47 235); X- and Y-zeolites (A. Barth et al., Z. Anorg. Allg. Chem. 521, (1985) pages 207–214); and a mordenite (EP-A-0 233 302); the entire contents of each of which are hereby incorporated by reference.

The co-oligomerization is expediently performed, depending on the catalyst, at 20 to 200° C. and at pressures of 1 to 100 bar. The reaction time (or contact time) is generally 5 to 60 minutes. The process parameters, in particular the type of catalyst, the temperature and the contact time are matched to one another in such a way that the desired degree of oligomerization is achieved. In the case of nonanols as desired target product, this is predominantly a dimerization. For this purpose, the reaction is preferably not run to full conversion, rather, conversion rates of 30 to 70% per pass are preferred. The optimum combinations of process parameters may be determined without difficulty by preliminary tests.

From the oligomerization mixture 3, in a $C_4$ separation stage 15, the residual gas 16 is separated off, in part recycled (as recycle gas 17) to the oligomerization stage 2 and in part ejected as off-gas 18. The recycling of a part of the residual gas 16 is preferred, because, as explained previously, the conversion in the oligomerization stage 2 may not be complete. The off-gas 18 is preferably taken off in order to discharge the minor amounts (12±3%) of n-butane/isobutane, which may be present in the $C_4$ fraction. Obviously, the off-gas 18 also contains butenes, more precisely predominantly by far n-butene, because the isobutene in any case present in a smaller amount in the $C_4$ fraction is oligomerized preferentially. The residual gas 16 is divided into recycle gas 17 and off-gas 18 in a ratio such that the content of n-butane and isobutane in the residual gas 16 does not increase too sharply. Advantageously, it is held below 70% by volume in the steady state.

The oligomers 19 remaining after separating off the residual gas 16 are fractionated in the oligomer separation stage 20 by distillation into dibutene 4, tributene (or dodecene) 21 and the residue 22. The tributene 21 is a desirable by-product. It can be hydroformylated, the hydroformylation products can be hydrogenated and the tridecanols thus obtained can be ethoxylated, by which means valuable detergent base materials are obtained. The dibutene 4 is directly suitable as starting material for the preparation of nonanols, especially since it is relatively linear because of the high proportion of n-butene in the $C_4$ fraction 1. When the particular properties of the nonanols from di-n-butene are of importance, the dibutene 4 can be separated in the fine distillation stage 23 into di-n-butene 6 and the diisobutenes 24 which, as more highly branched molecules, are lower boiling. The diisobutenes 24 can likewise be used for the preparation of plasticizer alcohols or, if appropriate after hydrogenation, as additive to motor gasoline.

Variant B

Figure 2:
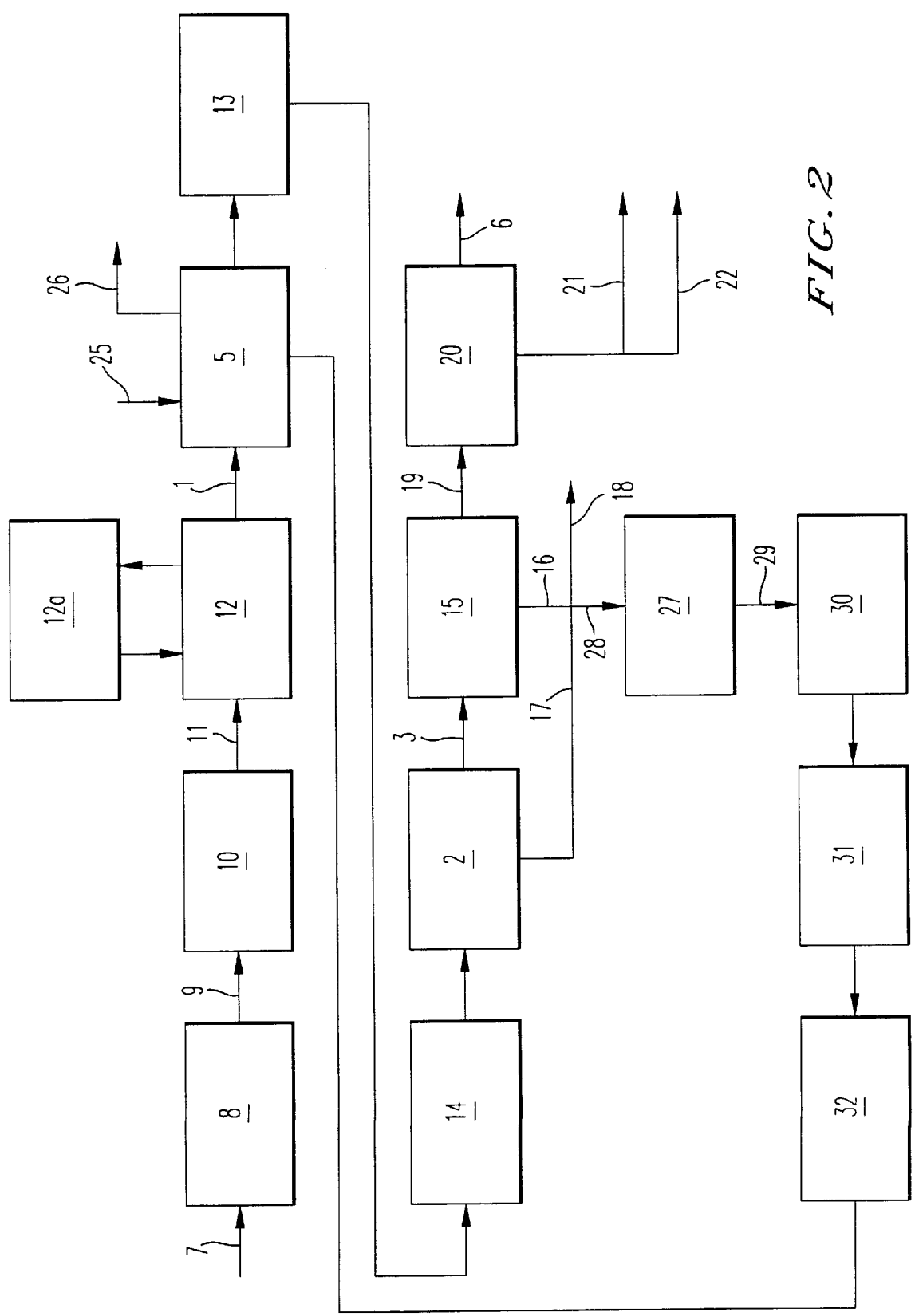
FIG. 2 is a block diagram which depicts Variant B.

Variant B, which corresponds to FIG. 2 describes a process in which the isobutene present in the $C_4$ fraction 1 is first reacted with an alkanol 25 in an etherification stage 5 to give an alkyl tert-butyl ether 26 and only the remaining n-butene is oligomerized, so that di-n-butene 6 is formed as sole dibutene. In a particular embodiment of the process variant B, an isomerization stage 27 is present, by means of which the n-butene which is unreacted in the oligomerization stage 2 is isomerized to give isobutene and this is recycled to the etherification stage 5.

In particular the latter embodiment of the process of variant B is distinguished by high flexibility. Variable amounts of di-n-butene and alkyl tert-butyl ether can be produced, depending on the market requirements.

In the variant B, isobutene is separated off from the $C_4$ fraction 1 in the etherification stage 5 by reaction with an alkanol 25 to give an alkyl tert-butyl ether 26. The reaction is virtually selective, since both isomers of n-butene are considerably less reactive than isobutene. In the oligomerization stage 2, only n-butene is then oligomerized, so that di-n-butene 6 is formed as sole dibutene.

Suitable alkanols 25 are primarily those having 1 to 6 carbon atoms, such as methanol, ethanol or isobutanol. Their reaction with isobutene is described, for example, in methyl tert-butyl ether, Ullmans Encyclopedia of Industrial Chemistry, Volume A 16, pages 543 ff, the entire contents of which are hereby incorporated by reference. The reaction takes place in liquid phase or in gas-liquid phase at a temperature of 50 to 90° C. and at a pressure which is established at the respective temperature. Expediently, a slight excess of alkanol is employed, which increases the selectivity of the reaction of the isobutene and represses its dimerization. The catalyst used is, for example, an acidic bentonite or a large-pored acid ion exchanger. From the liquid etherification mixture there is produced by distillation the alkyl tert-butyl ether 26 and, if appropriate, excess alkanol which can be recycled to the reaction.

Separating off the isobutene by reaction with an alkanol is particularly advisable if there is a use for the alkyl tert-butyl ether, in particular the methyl tert-butyl ether, as an octane-rating-improving additive to motor gasoline.

In a particular embodiment of variant B, an isomerization stage 27 is present, by means of which some of the n-butene is converted into isobutene. The additional isobutene is recycled to the etherification stage 5. In this manner the ratio of di-n-butene to alkyl tert-butyl ether can be varied and adapted to the requirements of the market.

The isomerization of olefins is also termed skeleton isomerization. The isomerization stage 27 is expediently assigned to the $C_4$ separation stage 15. The residual gas 16 containing up to 70% by volume of n-butane and isobutane is then divided into three part-streams: recycle gas 17, off-gas 18 and isomerization gas 28. The isomerization of n-butene to isobutene has been developed recently; an overview of the various processes is given in F. Nierlich, Recent Developments in Olefin Processing for Cleaner Gasoline, Oil Gas European Magazine, 1992, 4, pages 31 ff, the entire contents of which are hereby incorporated by reference. All processes have in common the fact that n-butene is mixed with steam and passed over an acid catalyst, e.g., an acid zeolite, at 500° C. to 600° C. under atmospheric pressure. During this, n-butene is isomerized to isobutene, expediently up to equilibrium, which, depending on the temperature, is 35 to 50% isobutene and 65 to 50% n-butene. Higher-boiling portions are separated off under pressure from the isomerization mixture 29 by a cycle water scrubber 30. The portions of the isomerization mixture 29 which are not condensed under these conditions and pass overhead as an azeotrope of (essentially) $C_4$ hydrocarbons and water are conducted to the separation stage 31, a column. There, an azeotrope of low-boilers and water passes overhead, and in the bottom phase, the $C_4$ hydrocarbons and small amounts of higher-boiling portions arise which were not condensed in the cycle water scrubber 30 and are separated off in the following separation stage 32, likewise, a column, as bottom product from the $C_4$ hydrocarbons passing overhead, which recirculate to the etherification stage 5.

The entire contents of German patent application 196 29 906.3, filed Jul. 24, 1996, are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for preparing butene oligomers from Fischer-Tropsch hydrocarbons, comprising:

separating from Fisher-Tropsch hydrocarbons a $C_4$ fraction containing butanes and butenes, said butenes comprising n-butenes and isobutene; and oligomerizing said butenes, without removing said butanes, with a catalyst to obtain an oligomerization mixture containing dibutene.

2. The process as claimed in claim 1, wherein said catalyst is selected from the group consisting of a homogeneous catalyst, a fixed catalyst, and a suspended catalyst.

3. The process as claimed in claim 1, wherein said Fischer-Tropsch hydrocarbons comprise ethylene, and said separating further comprises:

dimerizing the ethylene; and recycling the dimerized ethylene to said $C_4$ fraction.

4. The process as claimed in claim 1, wherein said $C_4$ fraction further comprises 1,3-butadiene, oxygen, and sulfur compounds, and wherein said process further comprises prior to said oligomerizing:

selectively hydrogenating the 1,3-butadiene to obtain butenes; and optionally removing the oxygen and sulfur compounds from the $C_4$ fraction with a molecular sieve.

5. The process as claimed in claim 4, wherein said molecular sieve has a pore diameter of 4–15 angstroms.

6. The process as claimed in claim 1, wherein said oligomerization mixture further comprises tributene.

7. The process as claimed in claim 1, further comprising:

separating said dibutene by fine distillation into di-n-butene and diisobutene.

8. A process for preparing butene oligomers from Fischer-Tropsch hydrocarbons, comprising:

separating from Fisher-Tropsch hydrocarbons a $C_4$ fraction containing butanes and butenes, said butenes comprising n-butenes and isobutene;

etherifying said isobutene by reacting with an alkanol over a first catalyst to obtain alkyl tert-butyl ether; and oligomerizing said n-butenes with a second catalyst to obtain an oligomerization mixture containing di-n-butene, wherein said $C_4$ fraction further comprises 1,3-butadiene, oxygen, and sulfur compounds, and wherein said process further comprises prior to said oligomerizing:

selectively hydrogenating the 1,3-butadiene to obtain butenes; and optionally removing the oxygen and sulfur compounds from the $C_4$ fraction with a molecular sieve.

9. The process as claimed in claim 8, wherein said di-n-butene is essentially the only dibutene that remains in the oligomerization mixture after said oligomerizing.

10. The process as claimed in claim 8, wherein said alkanol is a $C_{1-6}$ alkanol.

11. The process as claimed in claim 10, wherein said $C_{1-6}$ alkanol is selected from the group consisting of methanol, ethanol, and isobutanol.

12. The process as claimed in claim 8, wherein said first catalyst is an acidic bentonite catalyst or a large-pored acid ion exchanger.

13. The process as claimed in claim 8, wherein said second catalyst is selected from the group consisting of a homogeneous catalyst, a fixed catalyst, and a suspended catalyst.

14. The process as claimed in claim 8, wherein a portion of n-butenes that remain after said oligomerizing step are isomerized with a third catalyst to obtain an isomerization mixture containing isobutene; and said isobutene is recycled to said etherifying step.

15. A process for preparing butene oligomers from Fischer-Tropsch hydrocarbons, comprising:

separating from Fisher-Tropsch hydrocarbons a $C_4$ fraction containing butanes and butenes, said butenes comprising n-butenes and isobutene;

etherifying said isobutene by reacting with an alkanol over a first catalyst to obtain alkyl tert-butyl ether; and oligomerizing said n-butenes with a second catalyst to obtain an oligomerization mixture containing di-n-butene; and isomerizing with a third catalyst a portion of n-butenes that remain after said oligomerizing to obtain isobutene.

16. The process as claimed in claim 15, wherein said isomerizing comprises mixing said n-butenes with steam; and passing the mixture obtained over an acid catalyst at a temperature of 500–600° C.

17. The process as claimed in claim 16, wherein said acid catalyst is an acid zeolite.

18. The process as claimed in claim 15, wherein 50% of said n-butenes are isomerized to isobutene in said isomerizing step.

19. The process as claimed in claim 15, wherein after said isomerizing, said isobutene is recycled back to said etherifying step.

20. A process for preparing butene oligomers from Fischer-Tropsch hydrocarbons, comprising:

separating from Fischer-Tropsch hydrocarbons a $C_4$ fraction comprising n-butenes, isobutene, 1,3-butadiene, oxygen, and sulfur compounds;

selectively hydrogenating the 1,3-butadiene to obtain butenes;

etherifying said isobutene by reacting with an alkanol over a first catalyst to obtain alkyl tert-butyl ether;

optionally removing the oxygen and sulfur compounds with a molecular sieve; and oligomerizing said n-butenes with a second catalyst to obtain an oligomerization mixture containing di-n-butene.

21. A process for preparing butene oligomers from Fischer-Tropsch hydrocarbons, comprising:

separating from Fischer-Tropsch hydrocarbons a $C_4$ fraction comprising n-butenes, isobutene, 1,3-butadiene, oxygen, and sulfur compounds;

etherifying said isobutene by reacting with an alkanol over a first catalyst to obtain alkyl tert-butyl ether;

selectively hydrogenating the 1,3-butadiene to obtain butenes;

removing the oxygen and sulfur compounds with a molecular sieve; and oligomerizing said n-butenes with a second catalyst to obtain an oligomerization mixture containing di-n-butene.

* * * * *